United States Patent
Martinez et al.

(10) Patent No.: US 6,692,834 B1
(45) Date of Patent: Feb. 17, 2004

(54) METHOD FOR COATING IMPLANTABLE DEVICES

(75) Inventors: Gonzalo Martinez, Mendota Heights, MN (US); Catherine E. Taylor, Minneapolis, MN (US); Kenneth W. Keeney, Forest Lake Township, MN (US); Markus Haller, Begnins (CH)

(73) Assignee: Medtronic, Inc., Minneapolis, MN (US)

(*) Notice: Subject to any disclaimer, the term of this patent is extended or adjusted under 35 U.S.C. 154(b) by 361 days.

(21) Appl. No.: 09/340,441

(22) Filed: Jun. 28, 1999

(51) Int. Cl.[7] ............... B32B 9/04; C08J 7/18
(52) U.S. Cl. ............... 428/448; 427/2.24; 427/2.25; 427/2.26; 427/488; 427/489; 427/491; 427/534; 427/535; 427/536; 427/538
(58) Field of Search ............... 428/448; 427/489, 427/488, 491, 534, 535, 536, 538, 2.24, 2.25, 2.26

(56) References Cited

U.S. PATENT DOCUMENTS

| 4,783,361 | A | * | 11/1988 | Ovshinsky et al. | 428/217 |
|---|---|---|---|---|---|
| 5,447,799 | A | * | 9/1995 | Loh et al. | 428/448 |
| 5,660,728 | A | | 8/1997 | Saaski et al. | 210/251 |
| 5,702,618 | A | | 12/1997 | Saaski et al. | 216/2 |
| 5,705,070 | A | | 1/1998 | Saaski et al. | 210/446 |
| 6,049,736 | A | * | 4/2000 | Stewart et al. | 607/116 |

* cited by examiner

Primary Examiner—Michael Barr
Assistant Examiner—Elena Tsoy
(74) Attorney, Agent, or Firm—Stephen W. Bauer; Eric R. Waldkoetter; Thomas F. Woods

(57) ABSTRACT

Coating an implantable device, such as micro electromechanical devices, is highly desirable to protect the implantable device from corrosion. A coating method includes depositing, preferably by plasma glow discharge, a reactant monomer on at least one surface of an implantable device, preferably at ambient temperature. The method will likely decrease the manufacturing time required for assembling such devices because completely assembled devices can be coated.

18 Claims, 1 Drawing Sheet

METHOD FOR COATING IMPLANTABLE DEVICES

FIELD OF THE INVENTION

The present invention relates to a method for coating micro electromechanical devices to provide coatings on such devices that are relatively corrosion-resistant and suitable for in vivo implantation, such as within a human body.

BACKGROUND

In many medical situations, it is desirable and often necessary to implant relatively small (micro) electromechanical devices for an extended period of time. For example, it may be desirable to continually administer fluid medication (either as a gas or a liquid) to a patient over an extended period of time. Examples of such treatments included the low dose continual administration of morphine for pain control, the administration of FUDR for cancer chemotherapy, the administration of baclofen for the treatment of intractable spasticity, and the like.

In such instances, a particularly desirable goal is to maintain a relatively constant level of medication in the patient's bloodstream. In order to accomplish this goal, relatively small fluid handling devices are implanted within a patient's body. However, both the medication and bodily fluids that may contact the micro fluid handling devices are typically corrosive. Thus, it is desirable to provide a corrosion-resistant layer to at least one surface of the micro fluid handling device to prevent or limit corrosion. For example, a nominal layer of a corrosion-resistant substance may be deposited on a substrate by sputtering by using an e-beam evaporator, where suitable corrosion-resistant substances may be silicon, gold, platinum, chrome, titanium, zirconium, and oxides of silicon or these metals. See, U.S. Pat. Nos. 5,660,728; 5,702,618; and 5,705,070 all to Saaski et al. It is described that the oxides may be formed by thermally oxidizing the corrosion-resistant substance in air after it has been applied to the substrate.

SUMMARY OF THE INVENTION

What is yet needed is a method for coating micro electromechanical devices that provides a relatively corrosion-resistant and electrically insulating coating on at least one surface of the device. Furthermore, it is highly desirable to coat the device at a relatively low temperature that will likely increase the fabrication process because substantially all of the device components and features can be assembled prior to coating the device. For example, in a typical device fabrication process, a corrosion-resistant coating is applied to individual components along the fabrication process but prior to complete assembly of the device. Because typical coating methods utilize relatively high temperatures, coating a completely assembled device is generally not possible because the relatively high coating temperatures tend to be detrimental to electrical components that, in turn, may ultimately adversely affect the functioning of the device.

As used herein, "corrosion" refers to a complex electrochemical degradation of a conductive material (such as a metal or a metal alloy) or a semiconductive material (such as silicon or carbon) due to a reaction between such materials and the environment, usually an aqueous electrolyte-containing environment that can be an acidic or basic (alkaline) environment. In general, a corrosion product of such a material is in the form of an oxide of the material, such as a metal oxide, silicon dioxide, and the like. While not wishing to be bound by any particular theory, it is believed that corrosion occurs when the material (such as copper or silicon) contacts an electolytic solution and a mini-electrochemical circuit is formed when a small amount of the material dissolves in the water and combines with oxygen or other dissolved species. In forming the mini-electrochemical circuit, an imbalance of electrons between the solution and the surrounding material creates a minute flow of electrons, or current. So long as a current is allowed to flow, the material will continue to deteriorate, resulting in degradation and even pitting of the material. An electrically insulating coating is one that prevents completion of the current in the "minielectrochemical curcuit."

Accordingly, one aspect of the present invention provides a method for coating an implantable device. Preferably, coating the implantable device is accomplished at a low temperature. "Low temperature," as used herein, means that an input of energy to increase the temperature during plasma deposition is not required. In accordance with the present invention, plasma deposition preferably occurs at about ambient temperature, typically from about 20EC to about 30EC.

A method for coating a surface of an implantable device preferably includes plasma pretreating at least one surface of the implantable device with an inert gas; providing the implantable device to a plasma reaction chamber; and plasma treating the at least one surface of the implantable device with a reactant monomer to form a coating thereon. "Inert" refers to relative chemical inactivity of a compound under ambient conditions however, under some plasma deposition conditions the "inert" compound may become reactive when a glow discharge of the compound is created.

Preferably, the reactant monomer is selected from the group consisting of a substituted or unsubstituted alkene, arene, silane, siloxane, and a combination thereof. More preferably, the reactant monomer is selected from the group consisting of ethylene, 2-methyl-1-pentene, xylene, divinylmethylsilane, hexamethyldisilane, tetramethylsiloxane, and a combination thereof.

A method in accordance with the present invention preferably includes plasma treating the at least one surface by creating a glow discharge of the reactant monomer in the presence of an inert gas. The inert gas is preferably selected from the group of argon, helium, nitrogen, neon, and a combination thereof. The reactant monomer is preferably in a ratio with the inert gas of about 3 parts to about 6 parts reactant monomer to about 1 part inert gas.

A method in accordance with the present invention preferably includes plasma treating the at least one surface by creating a glow discharge of the reactant monomer using a power of about 30 Watts to about 100 Watts for a time period from about 10 minutes or less. Preferably, the method includes a pressure within the reaction chamber of about 0.025 Torr to about 0.1 Torr.

In accordance with the present invention, plasma pretreating the at least one surface includes supplying the inert gas to the reaction chamber at a flow rate of about 2 sccm. Preferably, plasma pretreating the at least one surface includes a pressure in the reaction chamber of about 5 mTorr to about 15 mTorr. Plasma pretreating the at least one surface preferably includes generating a glow discharge of the inert gas using radio frequency (abbreviated herein "R.F.") power of about 100 Watts for a time of about 2 minutes or less.

Additionally, a method in accordance with the present invention may further include cleaning the at least one surface prior to plasma treating the at least one surface with a reactant monomer. Preferably, cleaning the at least one surface is accomplished prior to plasma pretreating the at least one surface.

Also in accordance with the present invention, the method may further include adding a polymer to the at least one surface having a coating thereon, wherein the polymer is selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof. The method may also include adding a bio-active compound to the at least one surface having a coating thereon. Preferably, the bio-active compound is selected from the group consisting of an antithrombotic agent, an antiplatelet agent, an antimitotic agent, an antioxidant, an antimetabolite agent, an anti-inflammatory agent, and a combination thereof.

An implantable device coated in accordance with the present invention can be selected from the group consisting of a pacemaker, a pacemaker-cardioverter-defibrillator, an implantable neurostimulator, a muscle stimulator, an implantable monitoring device, an implantable fluid handling device, a defibrillator, a cardioverter/defibrillator, a gastric stimulator, a drug pump, and a hemodynamic monitoring device.

Another aspect of the present invention provides an implantable device including at least one surface coating formed by the method described above. Preferably, the coating has a thickness of about 200Å to about 2000Å. In accordance with the present invention, the at least one surface can include a metal, a nonmetal, and a combination thereof.

Yet another aspect of the present invention provides an implantable device including at least one surface having a coating formed thereon from a compound selected from the group consisting of ethylene, 2-methyl-1-pentene, xylene, divinylemthylsilane, hexamethyldisilane, and tetramethylsiloxane.

As used herein, "reactant" monomer refers to a branched or unbranched hydrocarbon that can be plasma deposited on a substrate, preferably at a relatively low temperature. The hydrocarbon can be classified as an aliphatic monomer, a cyclic monomer, or it can include a combination of aliphatic and cyclic groups (e.g., alkaryl and aralkyl groups), wherein the hydrocarbon may include one or more heteroatoms, such as nitrogen, oxygen, sulfur, silicon, etc. In the context of the present invention, the term "aliphatic" means a saturated or unsaturated linear or branched hydrocarbon. This term is used to encompass alkyl, alkenyl, and alkynyl compounds, for example. The term "alkyl" means a saturated linear or branched hydrocarbon, including, for example, methane, ethane, isopropane, t-butane, heptane, dodecane, and the like. The term "alkenyl" means an unsaturated linear or branched hydrocarbon with one or more carbon-carbon double bonds, such as a vinyl-containing compound. The term "alkynyl" means an unsaturated linear or branched hydrocarbon with one or more triple bonds. The term "cyclic" means a closed ring hydrocarbon that is classified as an alicyclic, aromatic, or heterocyclic compound. The term "alicyclic" means a cyclic hydrocarbon having properties resembling those of aliphatic hydrocarbons. The term "aromatic" or "arene" compound means a mono- or polynuclear aromatic hydrocarbon.

A method in accordance with the present invention is suitable for any implantable device but is particularly well suited for micro eletromechanical devices, such as implantable pumps, filters, valves, cardiac pacesetters, and the like.

DETAILED DESCRIPTION

Figure 1:
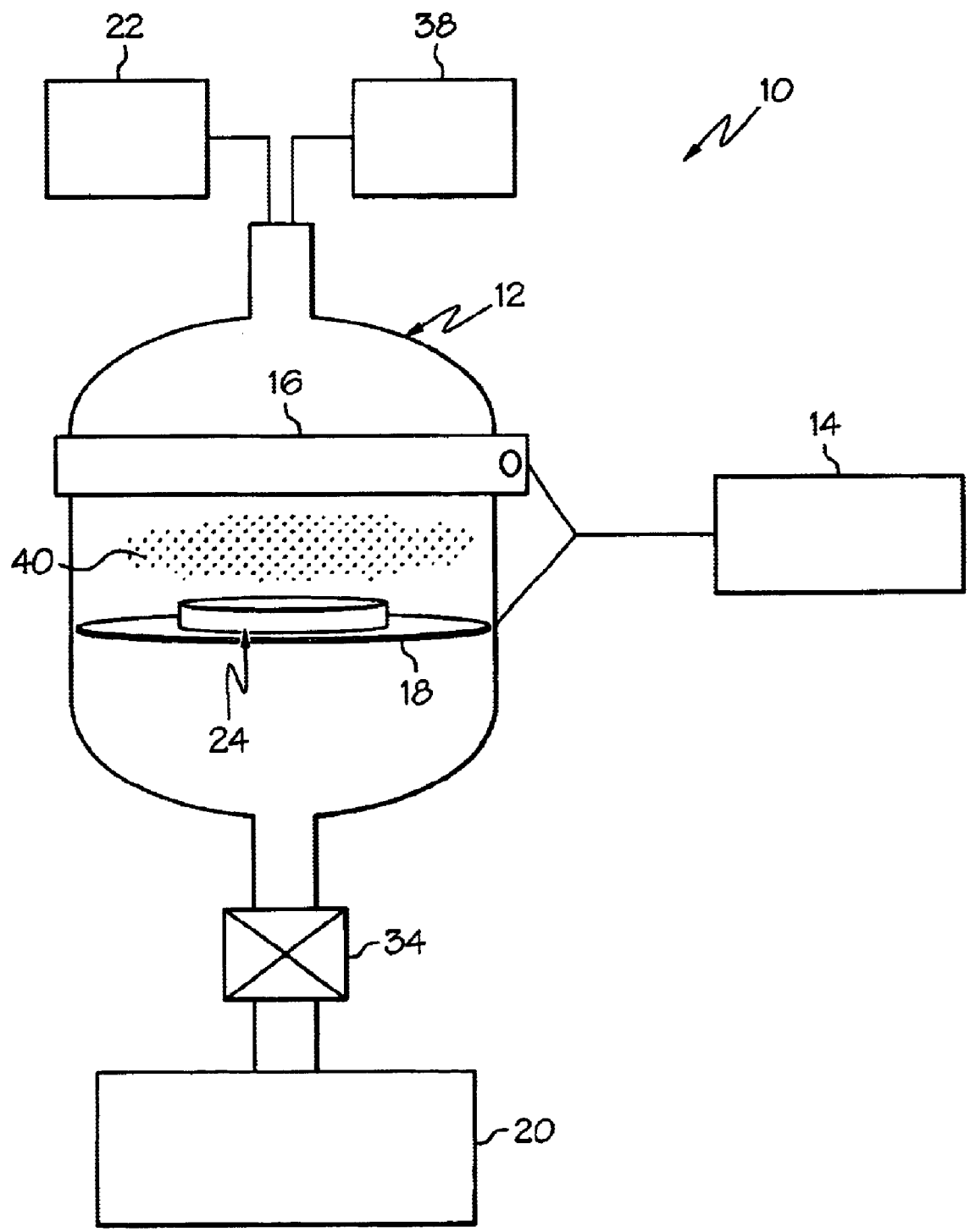
FIG. 1 is a schematic of an apparatus for use in a coating method in accordance with the present invention.

Coating at least one surface of an implantable device that provides a relatively corrosion-resistant coating on at least one surface of the device preferably includes plasma deposition of a reactant monomer, preferably a reactant monomer selected from the group consisting a substituted or unsubstituted alkene, arene, silane, siloxane, and a combination thereof. More preferably, the reactant monomer is selected from the group consisting of ethylene, xylene, 2-methyl 1-pentene, divinylmethylsilane, hexamethyldisilane, tetramethyldisiloxane, and a combination thereof.

Suitable plasma reactors are known in the art, examples of which are described by Yasuda, H., *Plasma Polymerization*, Academic Press (Orlando, Fla., 1985); and d'Agostino, R., *Plasma Deposition, Treatment, and Etching of Polymers*, Academic Press (San Diego, Calif., 1990). Typically, such plasma reactors use short wave energy (RF or microwave) to excite plasma.

In general, a plasma reactor for use in the present invention can include a glass reaction chamber that is fitted with a vacuum exhaust, gas inlets and at least one capacitively coupled electrode. In addition, the reactor is fitted with a pressure transducer and a mass flow controller for controlling and measuring the amount of gas being introduced into the reactor. The theory and practice of radio frequency (RF) gas discharge is explained in detail in 1) "Gas-Discharge Techniques For Biomaterial Modifications" by Gombatz and Hoffman, *CRC Critical Reviews in Biocompatibility*, Vol. 4, Issue 1 (1987) pp 1–42;2) "Surface Modification and Evaluation of Some Commonly Used Catheter Materials, I. Surface Properties" by Triolo and Andrade, *Journal of Biomedical Materials Research*, Vol. 17, 129–147 (1983), and 3) "Surface Modification and Evaluation of Some Commonly Used Catheter Materials, II. Friction Characterized" also by Triolo and Andrade, *Journal of Biomedical Materials Research*, Vol. 17, 149–165 (1983).

FIG. 1 illustrates in schematic form a plasma reactor 10 that can be employed in a method in accordance with the present invention. The plasma reactor 10 includes, in general, a vertical reaction chamber 12, R.F. power source 14 coupled across upper and lower electrodes 16 and 18, vacuum pump 20 and a reactant monomer source 22 in fluid communication with the reaction chamber 12. Preferably, the reactant monomer source 22 also includes a means for controlling the flow rate of the reactant monomer (not shown).

A substrate having at least one surface 24 to be coated is disposed on one electrode, for example, the lower electrode 18. Optionally, the electrode 18 can be brought to a suitable temperature by a heating/cooling unit (not shown) that may be located in close proximity to electrode 18 and electrically controlled by a temperature control unit (not shown). Preferably, a plasma deposition method in accordance with the present invention does not require the input of energy for heating or cooling, so that the deposition takes place at a relatively low temperature, more preferably ambient temperature (typically about 20EC to about 30EC). However, it will be recognized by those with ordinary skill in the art that although plasma deposition takes place at a relatively low temperature, the temperature of the surface so coated may increase slightly, typically to a temperature just slightly warmer than ambient temperature to the touch.

Optionally, a bellows (not shown) may be provided to adjust the spacing between the electrodes and, hence, controlling the confinement of the plasma 40. Preferably, a throttle valve 34 may be provided to control the pressure in the reaction chamber 12. The parameters that typically control the film characteristics formed from the reactant monomer include gas composition, gas flow rate, R.F. power, pressure, and temperature. Typically, the R.F. power can range from about 30 Watts to about 100 Watts, but is preferably at about 40 Watts for reactant monomer deposition. The pressure is typically about 0.025 Torr to about 1.0 Torr. Preferably, a glow discharge of the reactant monomer is created by using the R.F. power above for a period of time of about 10 minutes or less, more preferably, from about 15 seconds to about 5 minutes, and even more preferably from about 1 minute to about 4 minutes.

Preferably, the reactant monomer is introduced into the reaction chamber with an inert gas from source 38 that may be in fluid communication with the reaction chamber 12. An inert gas can be selected from the group of argon, helium, nitrogen, neon, and the like. Preferably, the inert gas is argon. Combinations of the inert gases can also be beneficial to make the initiation of discharge (i.e., generation of the plasma) easier. For example, argon can be added to neon in a minor amount that may improve plasma initiation.

The reactant monomer is preferably provided to the reaction chamber in a ratio with the inert gas of about 3 parts to about 6 parts, preferably about 3 parts to about 5 parts, reactant monomer to about 1 part inert gas. For example, the reactant monomer gas flow rate is preferably about 8 sccm to about 12 sccm, more preferably about 9 sccm to about 10 sccm, and the inert gas flow rate is preferably about 2 sccm. Of course, one skilled in the art will readily appreciate that the deposition rate of the reactant monomer depends on the gas composition and is directly proportional to the gas flow rate, power, pressure, and is inversely proportional to temperature so that one could empirically determine the optimum parameters, such as those indicated above, for desired film characteristics.

For example, in one embodiment, the operating pressure can be about 0.1 Torr. The reactant monomer can be supplied at a rate of about 10 sccm and an inert gas can be supplied at a rate of about 2 sccm. A glow discharge can be created by supplying R.F. power of about 40 Watts for a period of time of about 2 minutes. Preferably, the reactant monomer is selected from the group consisting of ethylene, 2-methyl-1-pentene, xylene, divinylmethylsilane, hexamethyldisilane, tetramethyldisiloxane, and a combination thereof. Preferably, the inert gas is argon.

A surface to be coated in accordance with the present invention is plasma pretreated to further prepare the surface prior to coating. For example, the surface can be pretreated in a plasma reactor, such as described above. An inert gas, such argon, can be supplied to the reaction chamber at a flow rate of about 2 sccm. The operating pressure can be about 5 mTorr to about 15 mTorr. A glow discharge can be created using an R.F. power of about 100 Watts for a time of about 2 minutes or less.

Preferably, prior to plasma depositing a reactant monomer on a device surface, the surface to be coated is thoroughly cleaned to remove any contaminating debris and the like. More preferably, the surface to be coated in accordance with the present invention is first cleaned and plasma pretreated prior to plasma depositing the reactant monomer. Conventional techniques can be used to adequately clean the surface, such as applying typical cleaning solvents (e.g., isopropyl alcohol, acetone, and the like) and/or ultrasonic cleaning in an aqueous solution, solvent cleaning, and the like. For example, the device to be coated can be placed in a conventional ultrasonic bath containing an aqueous detergent solution for cleaning and then subsequently rinsed to remove detergent prior to coating.

Although the foregoing was described with particular attention to the corrosion-resistance of a coating formed in accordance with the present invention, it is to be understood by those skilled in the art that such a coating can also be utilized in other applications. For example, a coating formed in accordance with the present invention can be used as an adhesion promoting primer to enhance adhesion of a second coating to the device, as a barrier layer for electronic contacts and devices, and a passivating layer.

For example, once a surface of a device has been coated as described above, a polymer can now be applied to the coated surface by conventional methods by dipping, spraying, or other application techniques. Polymers particularly suitable include a natural hydrogel, a synthetic hydrogel, silicone, polyurethane, polysulfone, cellulose, polyethylene, polypropylene, polyamide, polyimide, polyester, polytetrafluoroethylene (TEFLON), polyvinyl chloride, epoxy, phenolic, neoprene, polyisoprene, and a combination thereof. Additionally, a bio-active compound can be adhered to a surface coated in accordance with the present invention. The bio-active compound can be applied directly to the surface that has been plasma treated, as described above, or the surface that has been plasma treated and includes the polymer adhered thereto. A suitable bio-active compound can be selected from the group consisting of an antithrombotic agent, an antiplatelet agent, an antimitotic agent, an antioxidant, an antimetabolite agent, an anti-inflammatory agent, and a combination thereof. For example, one preferred bio-active compound is heparin. The subsequent addition of a polymer and/or a bio-active compound can be accomplished utilizing conventional techniques known in the art, such as described by Y. Ikada, "Surface Modification of Polymers for Medical Applications," *Biomaterials*, Vol. 15:725–736 (1994); E. A. Kulik, et al., "Peroxide Generation and Decomposition on Polymer Surface," *J. of Polymer Science: Part A: Polymer Chemistry*, Vol. 33:323–330 (1995); and K. Allm Ⓡr et al., *J. of Polymer Science*, Vol. 28:173–183 (1990), for example.

An implantable device may be any implantable device. For example, in the case where the implantable device is a pacemaker, the implantable device may be a pacemaker such as that described in U.S. Pat. No. 5,158,078 to Bennett, et al.; U.S. Pat. No. 5,312,453 to Shelton et al.; or U.S. Pat. No. 5,144,949 to Olson et al.

Implantable device may also be a pacemaker-cardioverter-defibrillator (PCD) corresponding to any of the various commercially-available implantable PCDs. For example, the present invention may be practiced in conjunction with PCDs such as those described in U.S. Pat. No. 5,545,186 to Olson, et al.; U.S. Pat. No. 5,354,316 to Keimel; U.S. Pat. No. 5,314,430 to Bardy; U.S. Pat. No. 5,131,388 to Pless; or U.S. Pat. No. 4,821,723 to Baker, et al.

Alternatively, an implantable device may be an implantable neurostimulator or muscle stimulator such as that disclosed in U.S. Pat. No. 5,199,428 to Obel, et al.; U.S. Pat. No. 5,207,218 to Carpentier, et al.; or U.S. Pat. No. 5,330, 507 to Schwartz, or an implantable monitoring device such as that disclosed in U.S. Pat. No. 5,331,966 to Bennett, et al.

Additionally, the implantable device may be micromachined devices such as implantable fluid handling devices for continuous administration of therapeutic agents including those for pain management, cancer chemotherapy, treatment of intractable spasticity, to name a few. Such devices are described in, for example, U.S. Pat. Nos. 5,705,070; 5,702,618; and 5,660,728 all to Saaski et al.

Further, for example, an implanted device may be a defibrillator, a cardioverter/defibrillator, a brain stimulator, a gastric stimulator, a drug pump, a hemodynamic monitoring device, or any other implantable device that would benefit from a coating for protection against corrosion. Therefore, the present invention is believed to find wide application in any form of implantable device. As such, the description herein making reference to any particular medical device is not to be taken as a limitation of the type of medical device that can be protected from corrosion as described herein.

In accordance with the present invention, at least one surface of an implantable device can be coated as described above. The at least one surface can be formed from a material selected from the group consisting of a metal (including alloys), a nonmetal, and a combination thereof. "Metal" refers to a group of compounds that tend to form positive ions when the compounds are in solution and include alkali metals, alkaline earth metals, transition metals, noble metals, rare metals, rare earth metals, to name a few. "Nonmetal" refers to a group of compounds that, in general, have very low to moderate conductivity and relatively high electronegativity and include germanium-, selenium-, and silicon-containing compounds, to name a few. Metals and nonmetals are both intended to include oxides and nitrides, and combinations thereof. For example, suitable materials that can be plasma treated in accordance with the present invention include gold, stainless steel, silicon, to name a few. The at least one surface may be located on the exterior surface, interior surface, or both, of an implantable device.

EXAMPLES

While surface modification methods and apparatuses in accordance with the invention have been described herein, the following non-limiting examples will further illustrate the invention.

In each of the following examples, silicon wafers having a size of about 1 $cm^2$ were coated as described below. Prior to plasma coating a reactant monomer on the surface of the wafer, each wafer was thoroughly cleaned. First, the wafers were cleaned by placing the wafers into a beaker containing acetone and soaked for 10 minutes at room temperature. The wafers were then removed from the acetone and placed in isopropyl alcohol and soaked for 10 minutes at room temperature. A beaker was filled with a cleaning solution of 30 parts D1 water to 1 part cleaning solution commercially available under the trade designation of ULTRAMET, from Buehler, Lake Bluff, Ill. Water was then placed in a conventional ultrasonic cleaner commercially available under the trade designation of ULTRASONIC CLEANER, from Branson Cleaning Equipment Co., Shelton, Conn., to a depth of at least ¼ the height of the beaker. The wafers were placed in the cleaning solution in the beaker. The beaker containing the wafers in the cleaning solution were placed into the ultrasonic cleaner. The ultrasonic cleaner was set for a cleaning time of 3 minutes.

The wafers were then removed from the cleaning solution and placed on a drying rack. The wafers were rinsed thoroughly with D1 water by rinsing 5 times with 2 quarts of DI water at ambient conditions. The wafers were then removed and placed on rice paper to dry for at least one half hour at ambient conditions.

Plasma pretreatment was applied directly to a cleaned silicon wafer surface. The wafer was placed in a plasma reaction chamber as described above and shown in FIG. 1. The wafers were placed on the lower electrode. The reaction chamber was evacuated to an initial pressure of less than about 5 mTorr. The operating pressure for plasma pretreatment was set at 11 mTorr and the reaction chamber was allowed to equilibrate for 15 minutes. Mass flow controllers were used to meter the argon gas into the reaction chamber at the rate of 2 sccm. A glow discharge was created by putting a 100 Watt RF power load on the electrodes for 1 minute exposure time.

All wafers, whether pretreated or not, were coated using a plasma reactor as described above and the parameters for reactant monomer deposition are recited for each example below.

Example 1

A silicon wafer that was not cleaned and pretreated as described above was placed in the plasma reaction chamber. The wafer was placed on the lower electrode. The reaction chamber was evacuated to a base pressure of 5 mTorr. The operating pressure was set 0.1 Torr and the reaction chamber was allowed to equilibrate for 15 minutes. Mass flow controllers were used to meter the ethylene flow at a rate of 15 sccm and the argon gas into the reaction chamber at the rate of 2 sccm. A glow discharge was created by putting a 100 Watt RF power load on the electrodes for 1 minute exposure time.

Under these conditions, a blue coating was visually observed on the wafer. The durability of the coated was evaluated by wiping the coated wafer surface with a laboratory tissue commercially available under the trade designation KIMWIPE (Kimberly Clark Corporation, Roswell, Ga.) with isopropyl alcohol. The coated surface scratched easily under these conditions.

Example 2

A cleaned and plasma pretreated silicon wafer, as described above, was placed in the plasma reaction chamber and plasma coated using the same conditions as described in Example 1.

Under these conditions, a blue coating was visually observed on the wafer. The durability of the coated was evaluated by wiping the coated wafer surface with a laboratory tissue commercially available under the trade designation KIMWIPE with isopropyl alcohol. The coated surface did not scratch under these conditions. To further evaluate durability, the coated wafer was cut in half, where a first half was placed in a 1N aqueous solution of sodium hydroxide and the second half was placed in a 1N aqueous solution of hydrochloric acid. Each half was soaked in the respective solution for 40 hours at room temperature. The coating on the first half of the wafer was observed with the naked eye as having many "pore-like" openings. The coating on the second half of the wafer lifted off the wafer surface after soaking in the hydrochloric acid solution.

Example 3

A cleaned and plasma pretreated silicon wafer was plasma coated with 2-methyl-1-pentene. After plasma pretreating the wafer for 1 minute, the RF power remained at 100 Watts and the operating pressure was increased to 0.1 Torr and the reaction chamber was allowed to equilibrate for 15 minutes. Thereafter, the RF power was decreased to 40 Watts. Mass flow controllers were used to meter the 2-methyl-1-pentene flow at a rate of 10 sccm and the argon gas into the reaction chamber at the rate of 2 sccm. A glow discharge was created by putting the 40 Watt RF power load on the electrodes for 2 minutes exposure time. A coating was produced on the wafer surface that had a thickness of 750Å.

Under these conditions, a smooth blue coating was visually observed on the wafer. Using a conventional dissecting microscope at a magnification of 10×, holes in the coating could not be detected. The durability of the coated was evaluated by wiping the coated wafer surface with a laboratory tissue commercially available under the trade designation KIMWIPE with isopropyl alcohol. The coated surface did not scratch under these conditions. To further evaluate durability, the coated wafer was placed in a 1N aqueous solution of sodium hydroxide for 16 hours at room temperature. The coating on the wafer was observed under 10× magnification as having many "pore-like" openings.

Example 4

A cleaned and pretreated silicon wafer was coated with 2-methyl-1-pentene as described in Example 3 with the only exception being that the glow discharge was created by putting the 40 Watt RF power load on the electrodes for 4 minutes exposure time. A coating was produced on the wafer surface that had a thickness of 575Å.

Example 5

A gold wafer was coated with 2-methyl-1-pentene as described in Example 3, except as follows. The gold wafer was placed in a plasma reaction chamber as described above and shown in FIG. 1. The wafers were placed on the lower electrode. The reaction chamber was evacuated to a base pressure of 5 mTorr. The operating pressure was set 0.03 Torr and the reaction chamber was allowed to equilibrate for 15 minutes. Mass flow controllers were used to meter the argon gas into the reaction chamber at the rate of 2 sccm. A glow discharge was created by putting a 100 Watt RF power load on the electrodes for 30 seconds exposure time.

After plasma pretreating the wafer for 30 seconds, the RF power remained at 100 Watts and the 2-methyl-1-pentent was added to the reaction chamber that was allowed to equilibrate for 5 minutes. Thereafter, the RF power was decreased to 40 Watts. Mass flow controllers were used to meter the 2-methyl-1-pentene flow at a rate of 9.6 sccm and the argon gas into the reaction chamber at the rate of 2 sccm. A glow discharge was created by putting the 40 Watt RF power load on the electrodes for 10 minutes exposure time. A coating was produced on the wafer surface that had a thickness of 1640Å.

Example 6

A cleaned and plasma pretreated silicon wafer was plasma coated with 2-methyl-1-pentene. After plasma pretreating the wafer for 1 minute, the RF power remained at 100 Watts and the operating pressure was increased to 0.1 Torr and the reaction chamber was allowed to equilibrate for 15 minutes. Thereafter, the RF power was decreased to 40 Watts. Mass flow controllers were used to meter the 2-methyl-1-pentene flow at a rate of 10 sccm and the argon gas into the reaction chamber at the rate of 2 sccm. A glow discharge was created by putting the 40 Watt RF power load on the electrodes for 2 minutes exposure time. A coating was produced on the wafer surface that had a thickness of 750Å.

Under these conditions, a smooth blue coating was visually observed on the wafer. Using a conventional dissecting microscope at a magnification of 10×, holes in the coating could not be detected. The durability of the coated was evaluated by wiping the coated wafer surface with a laboratory tissue commercially available under the trade designation KIMWIPE with isopropyl alcohol. The coated surface did not scratch under these conditions. To further evaluate durability, the coated wafer was placed in a 1N aqueous solution of sodium hydroxide for 16 hours at room temperature. The coating on the wafer was observed under 10× magnification as having many "pore-like" openings.

Example 7

A cleaned and plasma pretreated silicon wafer was plasma coated with tetramethyldisiloxane (TMDSO) under the same conditions as described in Example 6. A coating was produced on the wafer surface that had a thickness of 750Å.

Under these conditions, a smooth blue coating was visually observed on the wafer. Using a conventional dissecting microscope at a magnification of 10×, holes in the coating could not be detected. The durability of the coated was evaluated by wiping the coated wafer surface with a laboratory tissue commercially available under the trade designation KIM WIPE with isopropyl alcohol. The coated surface did not scratch under these conditions. To further evaluate durability, the coated wafer was placed in a 1N aqueous solution of sodium hydroxide for 16 hours at room temperature. The coating on the wafer was observed under 10× magnification as having many "pore-like" openings.

Example 8

A cleaned and plasma pretreated silicon wafer was plasma coated with divinylmethylsilane under the conditions described in Example 6. A coating was produced on the wafer surface that had a thickness of 750Å.

Under these conditions, a smooth blue coating was visually observed on the wafer. Using a conventional dissecting microscope at a magnification of 10×, holes in the coating could not be detected. The durability of the coating was evaluated by wiping the coated wafer surface with a laboratory tissue commercially available under the trade designation KIMWIPE with isopropyl alcohol. The coated surface did not scratch under these conditions. To further evaluate durability, the coated wafer was placed in a 1N aqueous solution of sodium hydroxide for 16 hours at room temperature. The coating on the wafer was observed under 10× magnification as having many "pore-like" openings.

The complete disclosures of all patents, patent applications, and publications are incorporated herein by reference as if individually incorporated. The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached thereto.

What is claimed is:

1. A method for coating a surface of an implantable device comprising:

plasma pretreating at least one surface of the implantable device with an inert gas;

providing the implantable device to a plasma reaction chamber; and plasma treating, in a single coating step, the at least one surface of the implantable device with a single reactant monomer to form a coating thereon while creating a glow discharge of the single reactant monomer using a power of about 30 Watts to about 100 Watts for a time period of about 10 minutes or less.

2. The method of claim 1, wherein the reactant monomer is selected from the group consisting of a substituted or unsubstituted alkene, arene, silane, siloxane, and a combination thereof.

3. The method of claim 2, wherein the reactant monomer is selected from the group consisting of ethylene, 2-methyl-1-pentene, xylene, divinylmethylsilane, hexamethyldisilane, tetramethylsiloxane, and a combination thereof.

4. The method of claim 1, wherein plasma treating the at least one surface comprises creating a glow discharge of the reactant monomer in the presence of an inert gas.

5. The method of claim 4, wherein the inert gas is selected from the group of argon, helium, nitrogen, neon, and a combination thereof.

6. The method of claim 4, wherein the reactant monomer is in a ratio with the inert gas of about 3 parts to about 6 parts reactant monomer to about 1 part inert gas.

7. The method of claim 1, wherein plasma pretreating the at least one surface comprises supplying the inert gas to the reaction chamber at a flow rate of about 2 sccm.

8. The method of claim 1, wherein plasma pretreating the at least one surface comprises a pressure within the reaction chamber of about 5 mTorr to about 15 mTorr.

9. The method of claim 1, wherein plasma pretreating the at least one surface comprises generating a glow discharge of the inert gas using an R.F. power of about 100 Watts for a time of about 2 minutes or less.

10. The method of claim 1 further comprising cleaning the at least one surface prior to plasma treating the at least one surface with a reactant monomer.

11. The method of claim 1, wherein plasma treating the at least one surface with the reactant monomer comprises a pressure within the reaction chamber of about 0.025 Torr to about 0.1 Torr.

12. The method of claim 1 further comprising adding a polymer to the at least one surface having the coating thereon, wherein the polymer is selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

13. The method of claim 1 further comprising adding a bio-active compound to the at least one surface having the coating thereon.

14. The method of claim 13, wherein the bio-active compound is selected from the group consisting of an antithrombotic agent, an antiplatelet agent, an antimitotic agent, an antioxidant, an antimetabolite agent, an anti-inflammatory agent, and a combination thereof.

15. The method of claim 1, wherein the implantable device is selected from the group consisting of a pacemaker, a pacemaker-cardioverter-defibrillator, an implantable neurostimulator, a muscle stimulator, an implantable monitoring device, an implantable fluid handling device, a defibrillator, a cardioverter/defibrillator, a gastric stimulator, a drug pump, and a hemodynamic monitoring device.

16. An implantable device comprising at least one surface coated by the method according to claim 1.

17. The implantable device of claim 1, wherein the coating has a thickness of about 200 Angstroms to about 2000 Angstroms.

18. The implantable device of claim 1, wherein the at least one surface comprises a metal, a nonmetal, and a combination thereof.

* * * * *